US007997553B2

(12) United States Patent
Sloan et al.

(10) Patent No.: US 7,997,553 B2
(45) Date of Patent: Aug. 16, 2011

(54) AUTOMATIC RETRACTABLE FLOOR SYSTEM FOR A ROTATING GANTRY

(75) Inventors: Terry Sloan, Bloomington, IN (US);
Earl W. Starks, Bloomington, IN (US)

(73) Assignee: Indiana University Research & Technology Corporati, Indianapolis, IN (US)

( * ) Notice: Subject to any disclaimer, the term of this patent is extended or adjusted under 35 U.S.C. 154(b) by 1067 days.

(21) Appl. No.: 11/813,923

(22) PCT Filed: Jan. 13, 2006

(86) PCT No.: PCT/US2006/001178
§ 371 (c)(1),
(2), (4) Date: Jul. 13, 2007

(87) PCT Pub. No.: WO2006/076545
PCT Pub. Date: Jul. 20, 2006

(65) Prior Publication Data
US 2008/0189859 A1    Aug. 14, 2008

Related U.S. Application Data

(60) Provisional application No. 60/643,951, filed on Jan. 14, 2005.

(51) Int. Cl.
*A47B 91/00*    (2006.01)
(52) U.S. Cl. ............... 248/346.02; 248/129; 248/346.01
(58) Field of Classification Search ............ 248/346.02, 248/346.01, 129, 170; 14/71.5, 71.7, 72.5
See application file for complete search history.

(56) References Cited

U.S. PATENT DOCUMENTS

| 622,666 | A | * | 4/1899 | Burwell ................. 182/223 |
| 1,595,007 | A | * | 8/1926 | Kindrat ................. 248/129 |
| 2,377,911 | A | * | 6/1945 | Warren ................. 108/54.1 |
| 2,405,535 | A | * | 8/1946 | Weiss ................. 108/54.1 |
| 3,247,931 | A | * | 4/1966 | Bunn ................. 188/5 |
| 3,977,333 | A | * | 8/1976 | Phillips ................. 108/54.1 |
| 4,804,162 | A | * | 2/1989 | Rice ................. 248/671 |
| 4,870,287 | A | | 9/1989 | Cole et al. |
| 5,097,132 | A | | 3/1992 | Plummer |
| 5,706,738 | A | * | 1/1998 | Rapeli ................. 108/54.1 |
| 5,855,035 | A | * | 1/1999 | Streeter et al. ............ 14/71.5 |
| 6,755,322 | B1 | | 6/2004 | Herzog et al. |
| 6,803,591 | B2 | | 10/2004 | Muramatsu et al. |

* cited by examiner

*Primary Examiner* — Amy J. Sterling
(74) *Attorney, Agent, or Firm* — Maginot, Moore & Beck LLP

(57) ABSTRACT

A movable floor system for use with a rotating gantry in a radiation treatment facility is provided that comprises a carriage assembly slidably supported within the gantry to maintain a substantially constant orientation while the gantry is rotating. An extendable/retractable panel assembly is supported on the carriage assembly that includes a plurality of non-movable floor panels and a like plurality of movable floor panels slidably mounted over corresponding ones of the non-movable panels. The movable panels are sized to span a distance between the carriage assembly and a fixed floor of the treatment room. Each of the movable panels has a platform surface for supporting a person for access to and from the patient table situated within the gantry. A control system coordinates the extension and retraction of the movable floor panels to prevent collisions with the radiation nozzle as it rotates during the patient treatment.

20 Claims, 15 Drawing Sheets

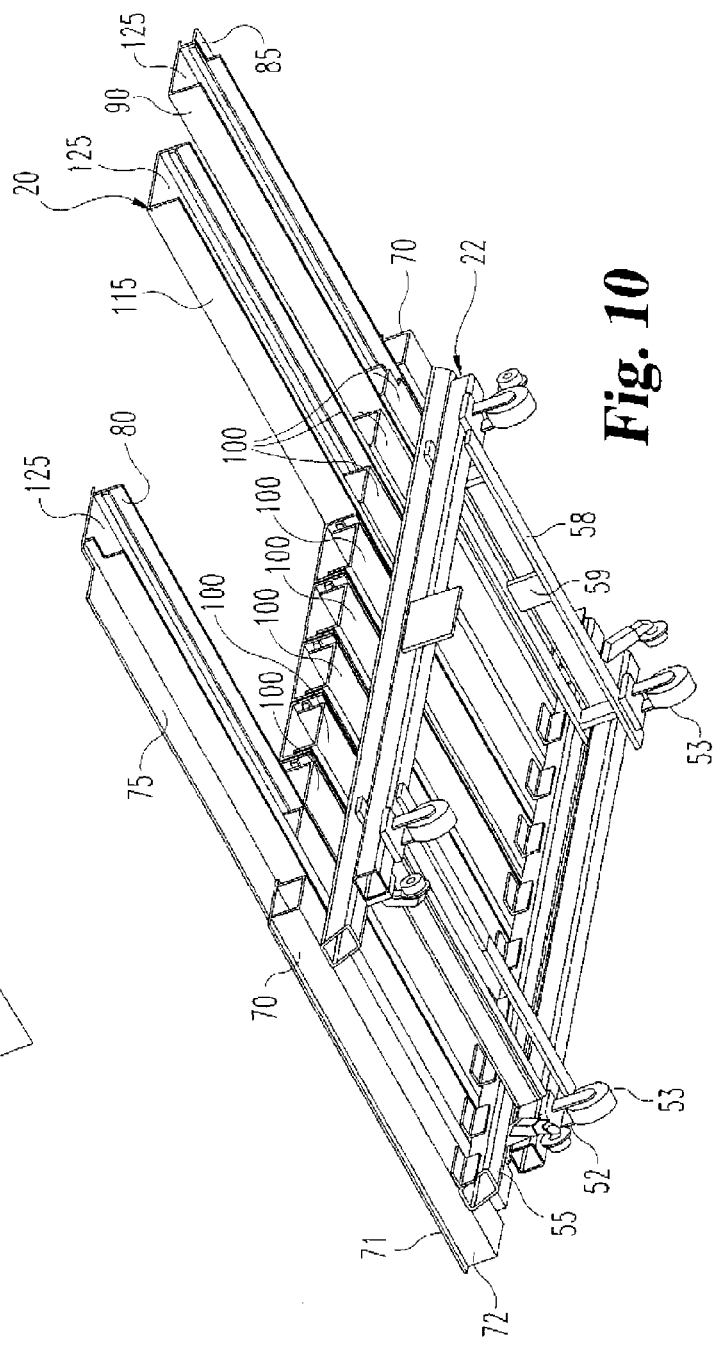
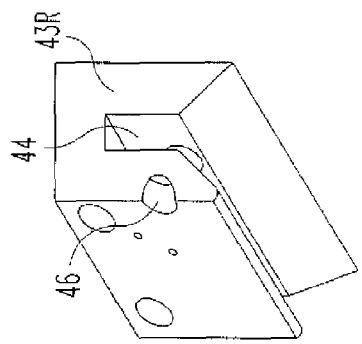
Fig. 9a
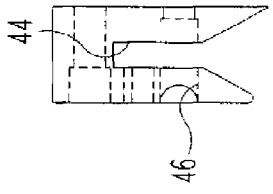
Fig. 9b
Fig. 10

AUTOMATIC RETRACTABLE FLOOR SYSTEM FOR A ROTATING GANTRY

REFERENCE TO RELATED APPLICATION

This application claims priority to co-pending U.S. Provisional application No. 60/643,951, filed on Jan. 14, 2005, the disclosure of which is incorporated herein by reference.

BACKGROUND OF THE INVENTION

1. Field of the Invention

The present invention relates to particle radiation therapy systems and, in particular, to the access floor surrounding a patient table within a rotating gantry system.

2. Description of the Related Art

Particle radiation therapy involves coordinating complex systems and devices to enable targeting of specific cancerous regions of a patient. In particular, proton beam therapy utilizes one or more precisely aligned particle streams to irradiate cancer or tumor cells. The energized protons disrupt targeted cells or tissue so as to effectively halt the progression of the disease. In proton beam therapy, the patient must be accurately positioned with respect to the one or more beams so that the stream irradiates only the desired target region, otherwise the stream may damage healthy cells within the patient's body. Specific alignment in this manner requires numerous control systems to maintain accurate and precise dosage delivery to a plurality of patients during prescribed treatments.

As described in U.S. Pat. No. 4,870,287, a proton treatment facility generally comprises a proton energy source, an injector, an accelerator, a beam transport system, a switchyard, and a plurality of treatment stations so as to accommodate multiple patients. Each treatment station may comprise a plurality of treatment components such as treatment platforms, gantry structures, and patient monitoring components. Additionally, control and monitoring of the proton treatment facility may be directed by computer and hardware subsystems, which coordinate the activities of each treatment station using software configurable components.

Moreover, control system activities may include beam intensity management, beam position orientation and modification, digital imaging performance, safety condition monitoring, and various other treatment functions. Together these systems form a highly complex collection of hardware and software components. The complexity of the proton treatment facility may be further magnified by managing multiple treatment stations where additional requirements for system redundancy and selective control of each treatment station is required.

The preferred position for a patient is the supine position so as to preclude any deformation of the organs during treatment. Therapy must therefore allow accessibility from all sides and encompass the entire human body. For this reason, the generally known proton therapy devices, are designed so that the entire proton beam guiding device housing is rotatable through 360 degrees about a central axis around a patient table that is aligned with that central axis. A typical proton treatment room includes the treatment system 10 shown in FIGS. 1-2. In this system, a rotating gantry 12 supports a beam nozzle 14 contained within a support housing 15. Protons from a remote source are directed by beam deflectors to the nozzle 14 to effect treatment of a patient P (FIG. 2) supported on a patient table T. The rotating gantry is a very large structure, typically measuring 40 feet in diameter at its largest extent, and about 20 feet in diameter at the mouth of the gantry. The table T is cantilever supported within the mouth of gantry 12 so that the entire gantry structure and nozzle 14 can rotate a complete 360° around the patient.

Safety considerations dictate the need for a floor adjacent the patient table. Moreover, the floor provides access to the patient table by radiation treatment technologists and medical personnel during setup of the treatment facility, positioning of the patient on the table, and sometimes during a treatment. The presence of the massive rotating gantry 12 is at odds with the need for complete access around the patient table T within the rotating gantry structure. In particular, any platform or floor providing access to the patient table will necessarily interfere with the necessary rotation of the gantry about eh patient. There is a significant need for a floor assembly that can be used with a large rotating gantry facility to provide immediate patient access without interfering with the operation of the gantry.

SUMMARY OF THE INVENTION

In order to address the need for a highly functional floor around the patient table, the present invention contemplates a floor assembly that includes floor segments or panels that extend to mate with the fixed floor of the treatment room and that retract to allow passage of the nozzle as the gantry rotates. In accordance with certain aspects of the invention, the movable panels are capable of supporting the weight of one, and preferably two, average sized adults when fully extended. The floor assembly permits rotation of the gantry from −185° to the +185° about the patient by retracting the movable panels. The floor panels mechanically latch to the fixed treatment room floor when fully extended and cannot be unintentionally released by personnel or equipment moving across the floor panels.

A control system is provided that orchestrates the extension and retraction of all the movable floor panels to adhere to certain safety requirements. For instance, the control system prevents all of the movable floor panels from being in their retracted position at the same time and may also mandate that at least two moveable panels be extended and locked to the fixed treatment room floor at all times. The control system is preferably configured to automatically stop the extension or retraction of a floor panel at the onset of certain emergency events. In some embodiments, the control system automatically moves the necessary floor panels in conjunction with the movement of the gantry and radiation nozzle. The control system direct the retraction of selected floor panels as needed to permit line of sight between an X-ray tube and its associated DR panel. A manual override feature may be provided that can be activated at the control panel in the control room to allow direct control over the extension or retraction of any of the movable floor panels. The control system may also be configured to that movement of a selected floor panel is inhibited until the pending movement is acknowledged at the control panel, except in the case of an emergency movement.

The control system preferably includes software that evaluates a gantry move to determine whether and which floor panels must be retracted or extended and when the movement must occur to permit passage of the nozzle. As a consequence, the gantry is provided with position sensors that are read by the control system to determine the angular position of the gantry, and particularly of the nozzle, at all times. However, control of gantry rotation is not disturbed by the control system for the present invention, meaning that the radiation technologist maintains direct control of the gantry rotation. A user interface is preferably provided that graphically displays the planned movement of the movable floor panels with respect to the gantry rotation. This user interface may also include a remote activation device held by medical personnel near the patient table that is only enabled after the display has been acknowledged by a technologist at the control panel once the technologist has determined that no equipment or personnel will be harmed by the floor movement or the gantry rotation. Enablement of the remote device then allows the medical personnel at the patient table to activate the floor movement sequence.

It is one object to provide a floor assembly that can be used with a rotating gantry and radiation nozzle system at a radiation treatment facility. It is a further object that the floor assembly be controllable to ensure adherence to certain safety protocols while also ensuring that no collisions will occur between the nozzle and the floor assembly as the gantry rotates.

One benefit of the movable floor system of the present invention is that it allows complete access to both sides of a patient table within a rotating gantry structure. Another benefit is that access to the patient table is always maintained by controlled extension and retraction of the movable floor panels. Other objects and benefits of the invention will become apparent from the following written description taken together with the accompanying figures.

DESCRIPTION OF THE FIGURES

FIG. 6b is a side view of the latch beam shown in FIG. 6a.

FIG. 7b is top view of the center latch shown in FIG. 7a.

FIG. 8b is a side view of the left side latch shown in FIG. 8a.

FIG. 9a is side perspective view of a right side latch that is mounted to the latch beam shown in FIGS. 6a-b.

FIG. 9b is a side view of the right side latch shown in FIG. 9a.

FIG. 10 is an enlarged bottom perspective view of a carriage assembly and floor assembly of the retractable floor system shown in FIGS. 3-4.

FIG. 11a is an enlarged bottom perspective view of the carriage assembly shown in FIG. 10 with two floor panel components mounted thereon.

FIG. 11b is an enlarged perspective view of the trolley wheel assembly in the carriage assembly shown in FIG. 11a.

FIG. 11c is an enlarged perspective view of the latch mechanism at one end of an extended center upper panel of the carriage assembly shown in FIG. 11a.

FIG. 11d is an enlarged perspective view of the latch mechanism at one end of a retracted center upper panel of the carriage assembly shown in FIG. 11a.

FIG. 11e is an enlarged perspective view of the cylinder mounting bracket arrangement of a center lower channel beam of the carriage assembly shown in FIG. 11a.

FIG. 12 is a top perspective view of a lower weldment forming part of the carriage assembly shown in FIG. 11a.

FIG. 13 is top perspective view of an upper weldment forming part of the carriage assembly shown in FIG. 11a.

FIG. 14b is an end view of the wing lower channel beam shown in FIG. 14a.

FIG. 15 is top perspective view of a left wing supported by the wing lower channel beam shown in FIG. 14a.

FIG. 16b is an end view of the left upper channel beam shown in FIG. 16a.

FIG. 17a is a top perspective view of a right wing supported by the wing lower channel beam shown in FIG. 14a.

FIG. 17b is a side view of the right wing shown in FIG. 17a.

FIG. 19b is a top view of the center lower channel beam shown in FIG. 19a.

FIG. 19c is a side view of the center lower channel beam shown in FIG. 19a.

FIG. 19d is an end view of the center lower channel beam shown in FIG. 19a.

FIG. 20b is an end view of the center upper channel beam shown in FIG. 20a.

FIG. 24b is a side view of the latch member shown in FIG. 24a.

FIG. 26b is a bottom perspective view of the right tongue plate shown in FIG. 26a.

FIG. 28 is an enlarged perspective view of a trolley wheel assembly that is mounted to the lower weldment frame as shown in FIGS. 10-11a.

DESCRIPTION OF THE PREFERRED EMBODIMENT

Figure 1:
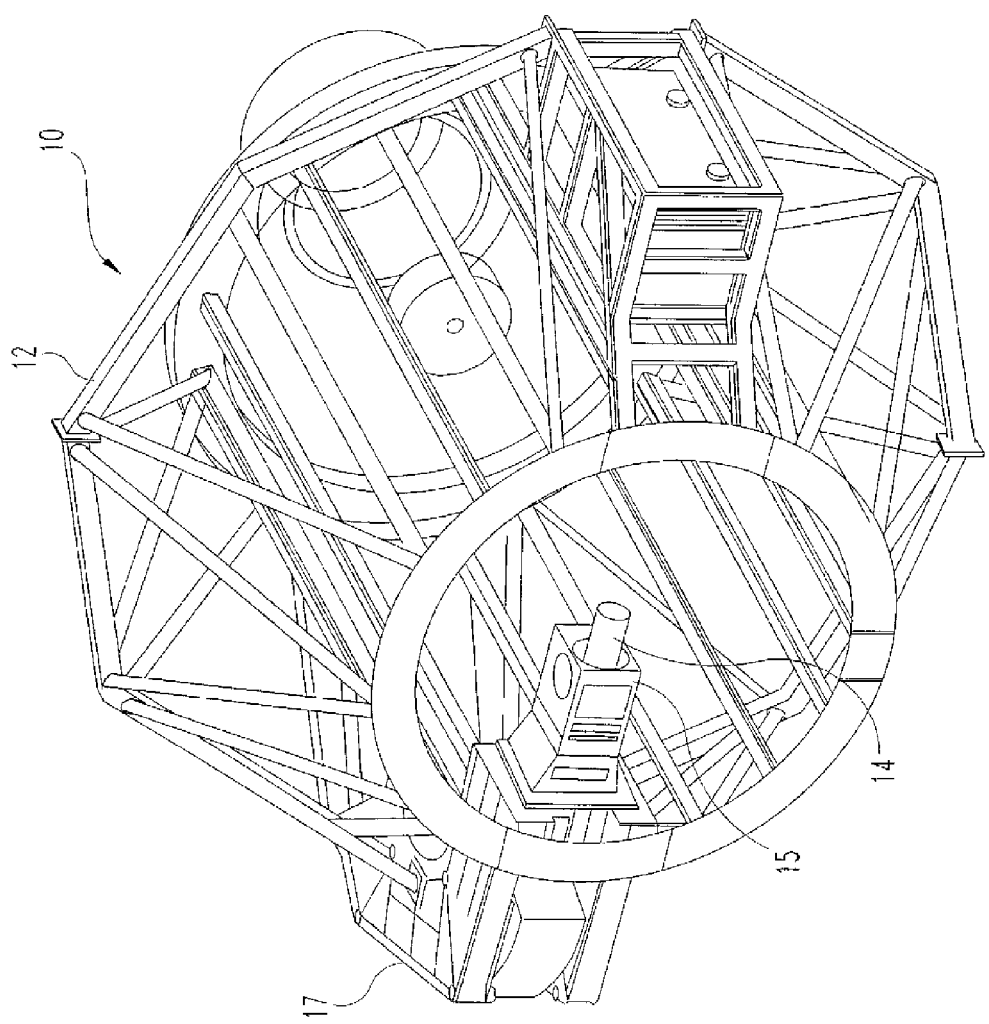
FIG. 1 is a perspective view of a radiation treatment system using a rotatable gantry.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 2:
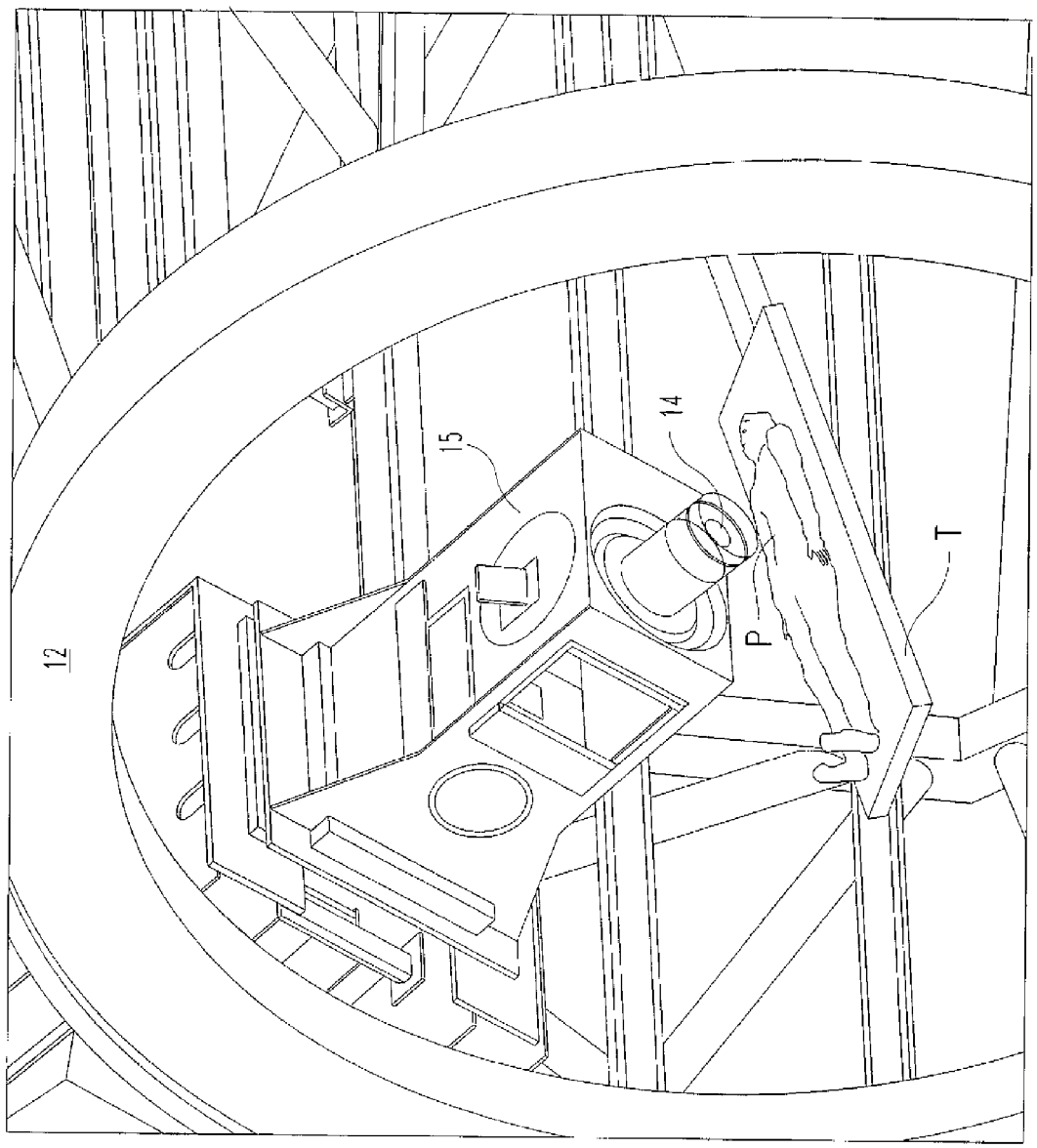
FIG. 2 is an enlarged perspective view of a patient within the gantry enclosure.
Figure 3:
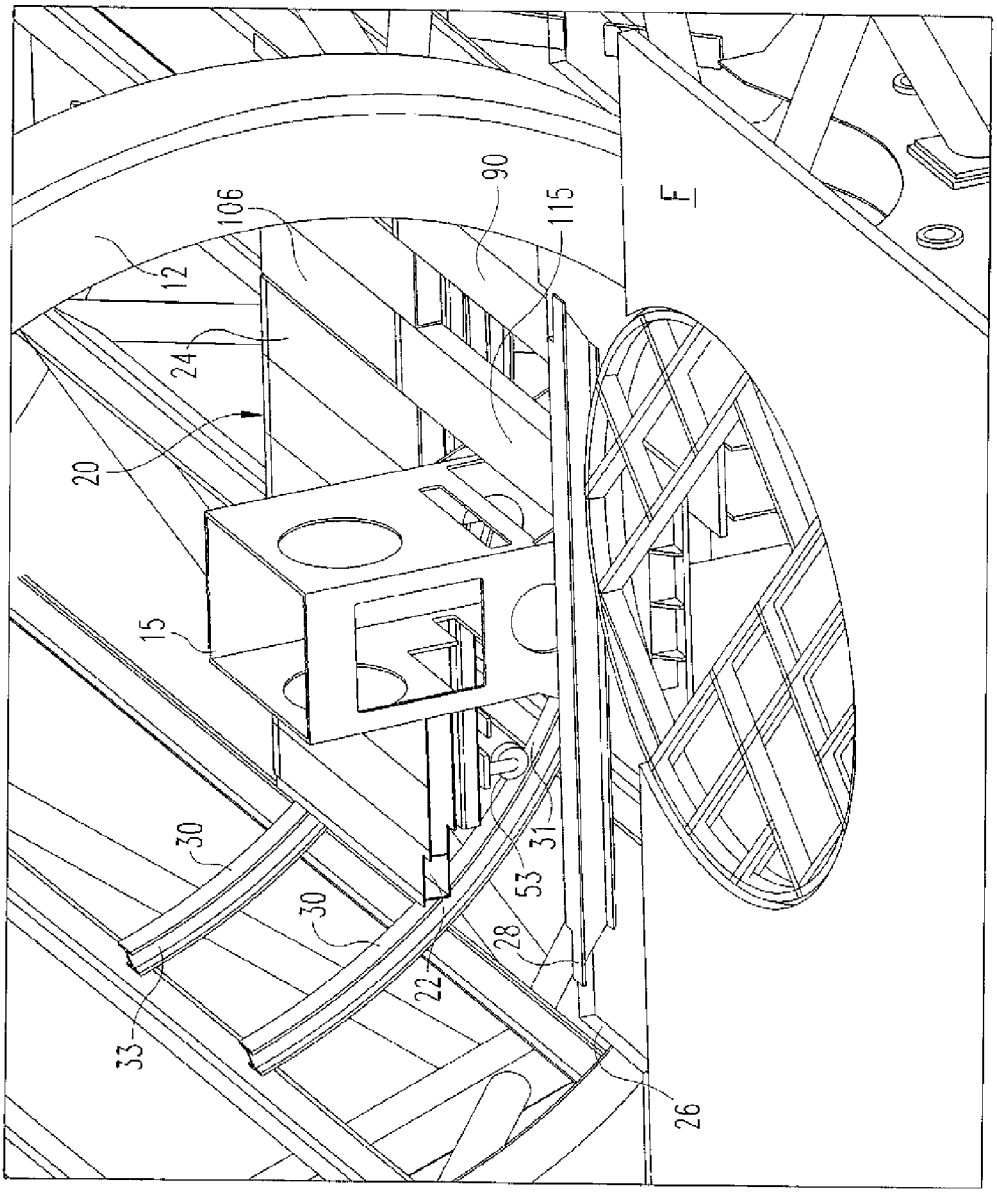
FIG. 3 is an enlarged perspective view of a rotatable gantry with the retractable floor system of the present invention.
Figure 4:
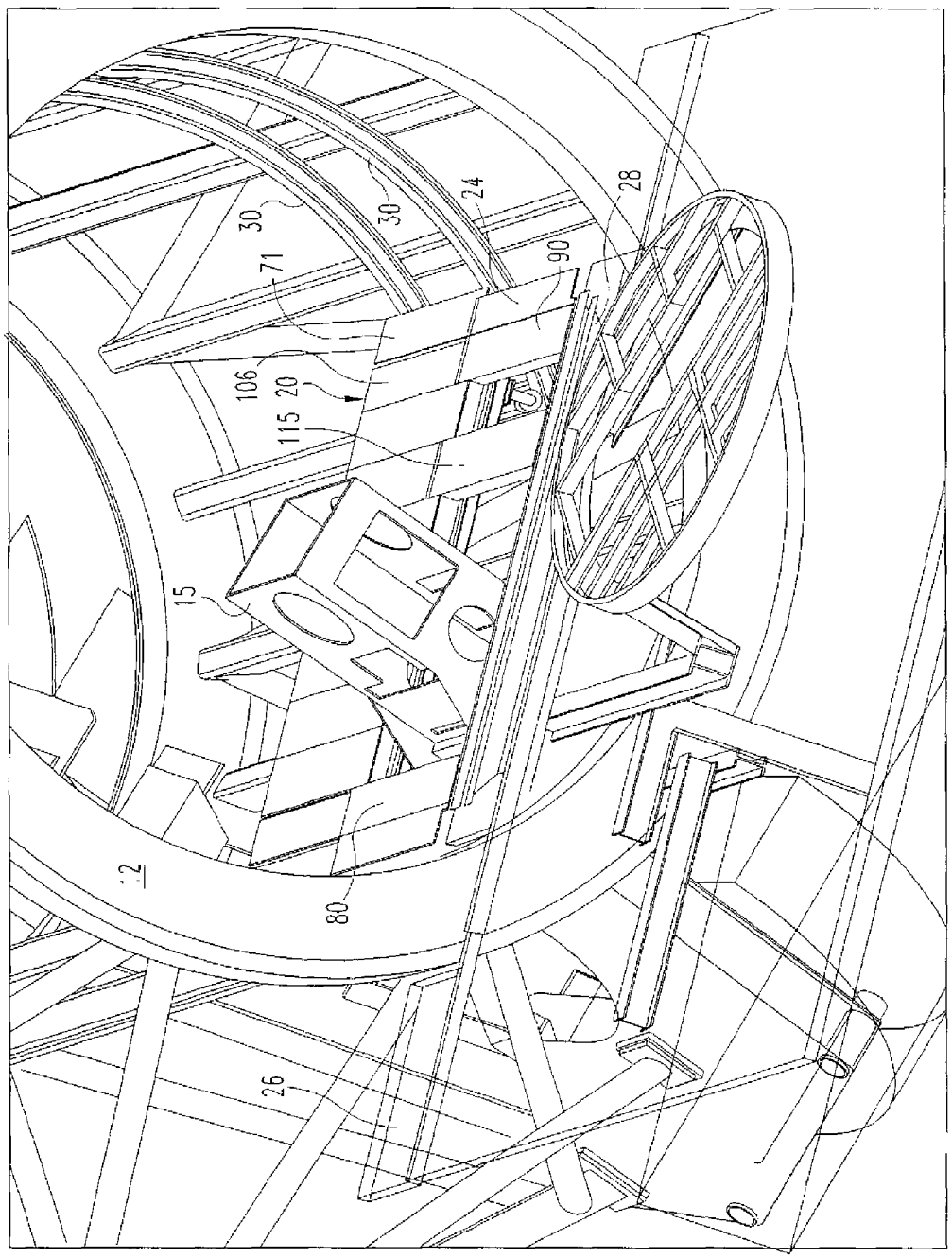
FIG. 4 is an enlarged perspective view of the gantry and floor system shown in FIG. 3 with the nozzle rotated to a different position.

As shown in FIGS. 3-4, the present invention contemplates a movable floor system 20 that is supported on a carriage assembly 22. The carriage assembly is supported relative to the gantry 12 so that the floor system 20 maintains its neutral horizontal position even as the gantry is rotated. The floor system 20 includes an extendable panel assembly 24 that controls the extension and retraction of various movable panels relative to several non-movable panels that are arranged at one end of the patient table (see table T in FIGS. 1-2). The patient table is not depicted in FIGS. 3-4 for clarity; however, it is know that the table extends along the rotation axis of the gantry 12 directly above the nozzle support structure 15 in FIG. 3. It can thus be appreciated that the floor assembly 20 is situated at the end of the table within the gantry enclosure. The extendable panel assembly extends part of the floor surface within the gantry enclosure to mate with the fixed floor F of the radiation treatment room, as represented by the floor panel 80, 90 and 115 in FIGS. 3-4.

Figure 5:
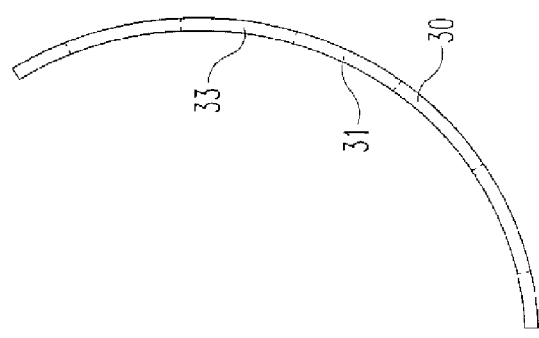
FIG. 5 is an end view of one of a plurality of floor rails mounted to the gantry as part of the retractable floor system shown in FIGS. 3-4.

As shown in FIG. 3, the carriage assembly 22 is supported on rollers 53 which ride along the rolling surface 31 of floor rails 30. The floor rails 30 are preferably 120° beam segments, as shown in FIG. 5, so that three such beam segments are combined to encircle the interior of the gantry 12. (Note that only one such segment is shown in FIGS. 3-4). Two sets of floor rails 30 are mounted to the gantry spaced apart by approximately the width of the carriage assembly 22. Although is contemplated that three segments combine to form each rail, any number of segments may be used depending upon the configuration of the gantry 12 and other construction considerations.

Figure 6A:
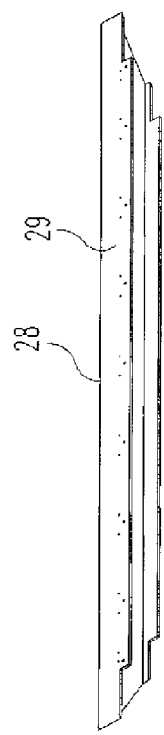
FIG. 6a is side perspective view of a latch beam mounted to the gantry as part of the retractable floor system shown in FIGS. 3-4.
Figure 6B:
Figure 7A:
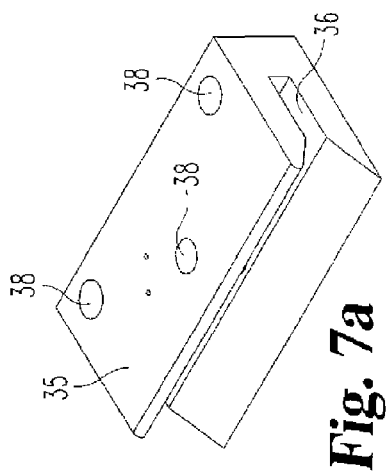
FIG. 7a is front perspective view of a center latch that is mounted to the latch beam shown in FIGS. 6a-b.
Figure 7D:
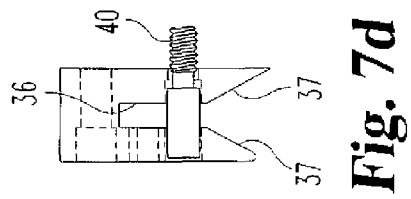
FIG. 7d is side view of the center latch shown in FIGS. 7a-c.
Figure 7B:
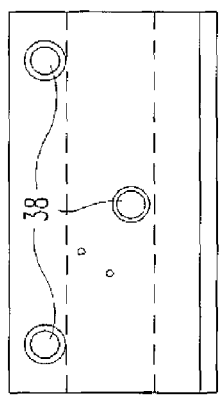
Figure 7C:
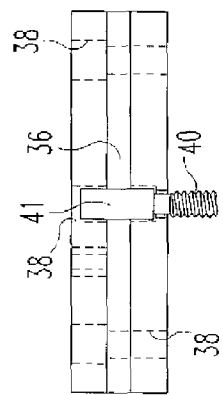
FIG. 7c is side view of the center latch shown in FIGS. 7a-b.

The interface to the fixed floor F is provide via a latch beam 28 mounted to the end of a floor extension 26 (FIG. 3). The floor extension 26 can be part of the fixed floor F or can be separately engaged to the floor F to form a continuous floor surface projecting into the mouth of the gantry 12. Of course, the extension 26 is sized so as not to interfere with the rotation of the gantry around the extension. The latch beam 28 includes a latch mounting flange to which a plurality of latches 35 and 43 (FIGS. 7a-9b) are mounted at bolt locations 29a (FIG. 6b). As shown in FIG. 6b, nine such bolt locations may be provided to support nine latches corresponding to nine movable floor panels of the extendable panel assembly 24. The latches include a plurality of center latches 35 (FIGS. 7a-d) that are mounted to the center portion of the latch beam 28, a left end latch 43L (FIGS. 8a-b) and a right end latch 43R (FIGS. 9a-b). The latches 35, 43L and 43R are similarly configured to define tongue slots 36, 44 and mounting bolt bores 38, 46. One of the mounting bolt bores in each latch is configured to receive a catch bolt 40, as shown in FIGS. 7c-d.

Figure 22:
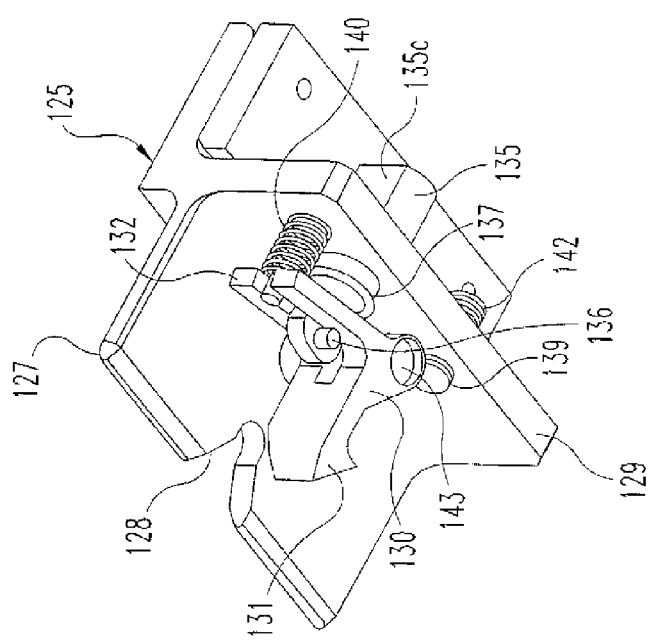
FIG. 22 is an enlarged bottom perspective view of a latch mechanism that is mounted to the upper channel beams shown above for engagement to the latches shown in FIGS. 7a-9b.

The catch bolt 40 includes an enlarged or elongated head portion 41 that extends into the tongue slot 36, 44, for engagement by a mating latch (see FIG. 22). As described herein, the latches positively lock a movable floor panel when it is extended to bridge the space between the floor assembly 20 and the fixed floor F (or more accurately the floor extension 26 and latch beam 28).

Additional details of the floor assembly 20 and carriage assembly 22 are shown in FIG. 10 and FIGS. 11a-e. The carriage assembly 22 is formed by a lower weldment frame 50 that is preferably constructed of tubular members 51 and cross beams 54 to form a rectangular construct (see FIG. 12). The tubular members 51 include roller supports 52 mounted at the opposite ends of the members. The roller supports carry rollers 53 that move along the rolling surface 31 of the floor rails 30. The rollers may be formed of high density polyurethane or other material that is capable of supporting the floor assembly and that is sufficiently strong to resist pitting. The rollers are carried by the roller supports by way of an axle and bushing or with a known bearing arrangement.

Figure 11:
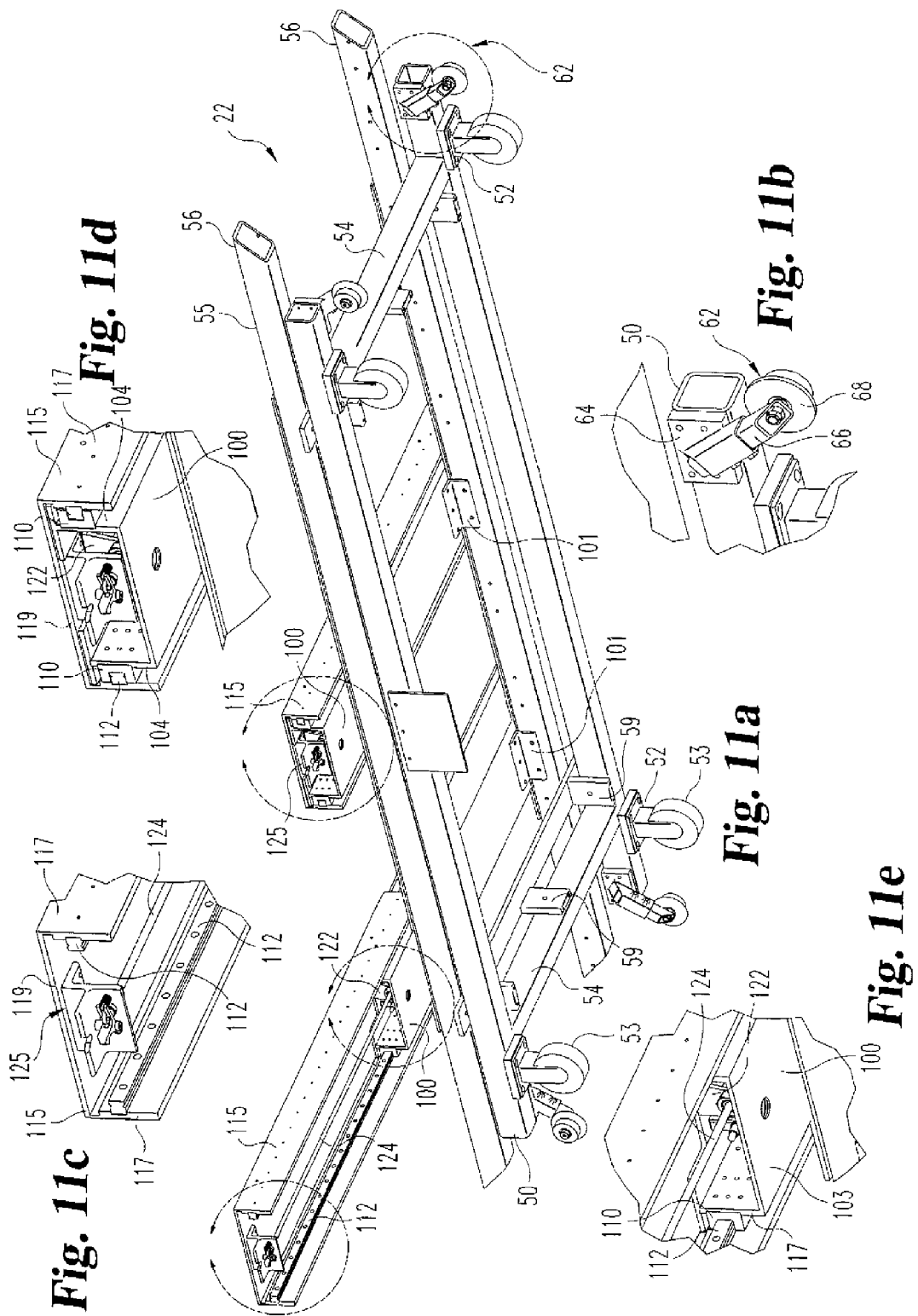
Figure 12:
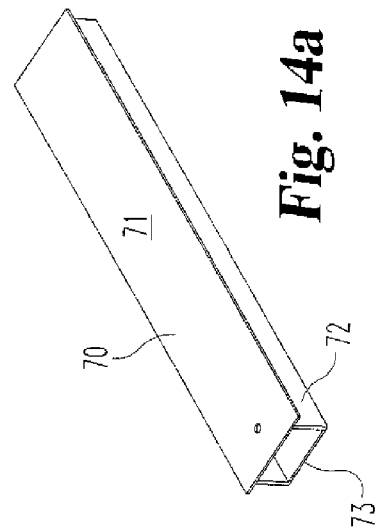
Figure 28:
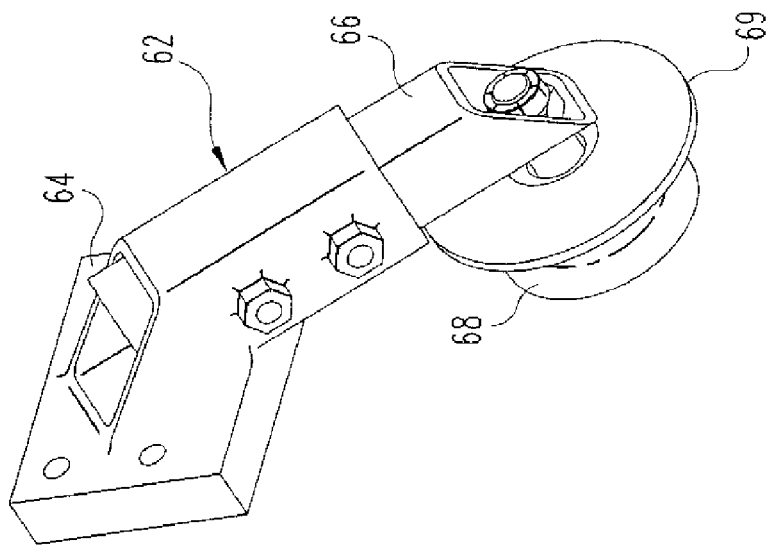
Figure 27:
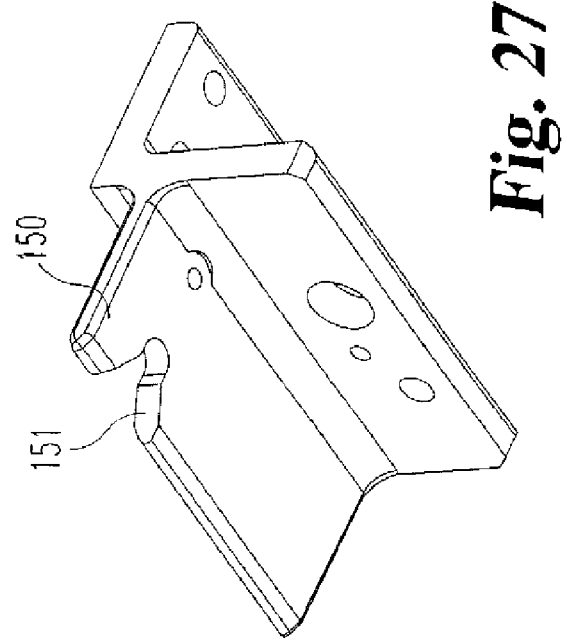
FIG. 27 is a bottom perspective view of a left tongue plate that forms part of a latch mechanism similar to that shown in FIG. 22.

In order to keep the floor assembly 20 on track with the floor rails, trolley wheel assemblies 62 (FIG. 28) are mounted at the inboard aspect of the opposite ends of the tubular members 51 of the lower weldment frame 50. The assemblies 62 are offset from the rollers 53, as shown best in FIG. 11a, so that the wheels 68 of the assemblies 62 can contact the inside guide surface 33 (FIGS. 3,5) of the floor rails 30. Preferably, the wheels 68 include a flange 69 that helps maintain the wheels in contact with the floor rails. The rollers 53 and wheels 68 thus keep the carriage assembly 22 aligned with the floor rails. As shown in FIG. 28, the assemblies 62 include a mounting plate 64 that is mounted to the ends of the tubular members 51 (FIG. 11). An extension tube 66 is telescopically mounted to the mounting plate 64 so that the position of the wheel 68 can be adjusted for optimum contact with the side guide surface 33 of the floor rails.

Figure 13:
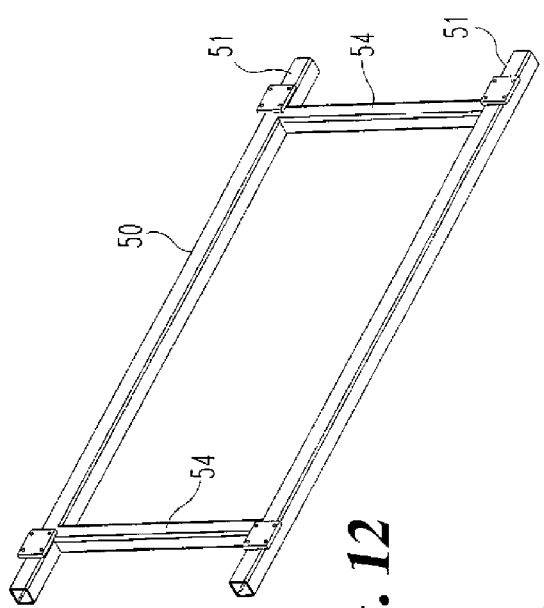

Returning to FIG. 10 and FIGS. 11a-e, the carriage assembly 22 also includes an upper weldment frame 55 that is mounted to the lower frame 50. As shown in FIG. 13, the upper frame 55 includes tubular members 56 that are welded to cross beams 58 to form a rectangular construct. The cross beams 58 may be welded to the tubular members 51 of the lower frame 50. Preferably, spacers are provided between the cross beams and the lower frame to ensure a level, horizontal orientation for the floor assembly supported on the upper frame. In addition, spacers 59 link the cross beams 54 of the lower frame to the cross beams 58 of the upper frame. The point of fixation of the spacers to the lower frame cross beams can be adjusted once a level orientation for the upper frame 55 has been established.

Figure 14A:
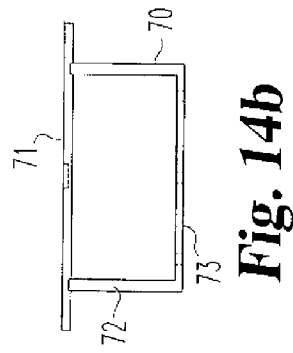
FIG. 14a is top perspective view of a wing lower channel beam forming part of the floor assembly shown in FIG. 10.
Figure 14B:
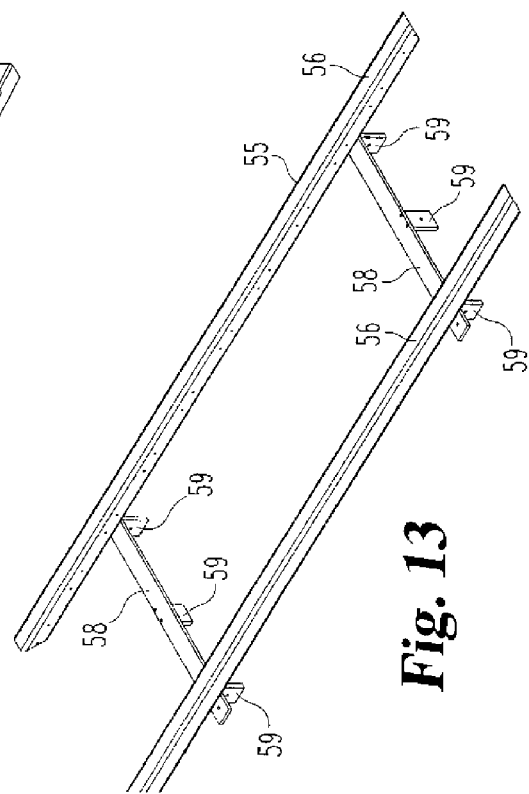

The extendable panel assembly 24 includes a plurality of moveable floor panels slidably supported on a like number of non-movable floor panels that are mounted to the upper weldment frame 55 of the carriage assembly 22. The non-movable floor panels include a pair of wing lower channel beams 70 (FIGS. 14a-b) that are positioned at opposite ends of the floor assembly, and a plurality of center lower channel beams 100 (FIGS. 19a-d) spanning the space between the wing lower channel beams. These non-movable components each define a non-moving panel surface 71, 106 that is exposed when a movable panel is extended. The lower channel beams 70, 100 are essentially of box beam construction so that the corresponding panel surfaces 71, 106 are sufficiently strong to support the weight of two adults. The two wing lower channel beams 70 include side walls 72 that combine with the support panel 71 and a bottom wall 73 to form the box beam construction. The center lower channel beams 100 include side walls 104 that combine with the support panel 106 and a bottom wall 102 to form the box beam. The bottom walls 73 and 102 provide a surface for mounting the wing and center lower channel beams to the upper weldment frame 55.

Figure 15:
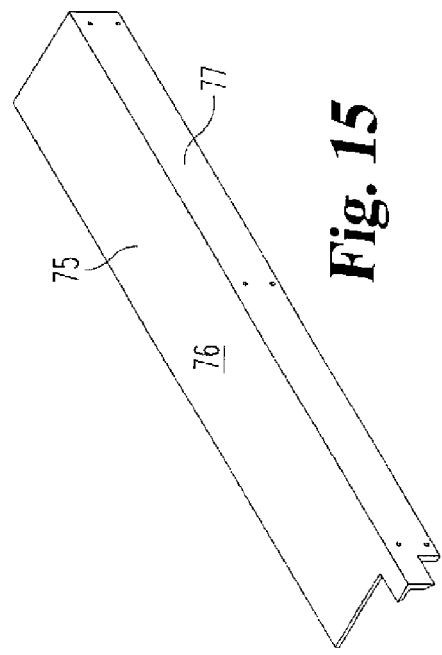

The movable portion of the floor assembly 20 includes several upper channel beam and wing beam components. A left wing panel 75 and a left upper channel beam 80 are connected and supported on the wing lower channel beam 70 at the left side of the floor assembly. The upper channel beam 80 includes an attachment flange 82 (FIG. 16a-b) to which an attachment flange 77 of the left wing 75 (FIG. 15) is engaged. The left wing panel 75 and upper channel beam 80 include support surfaces 76, 81, respectively that are capable of supporting a person when the movable portion is appropriately latched, as described in more detail herein. The right side components, including right wing 86 (FIGS. 17a-b) and right upper channel beam 90 (FIG. 18) are mirror images of the left side components.

Figure 16A:
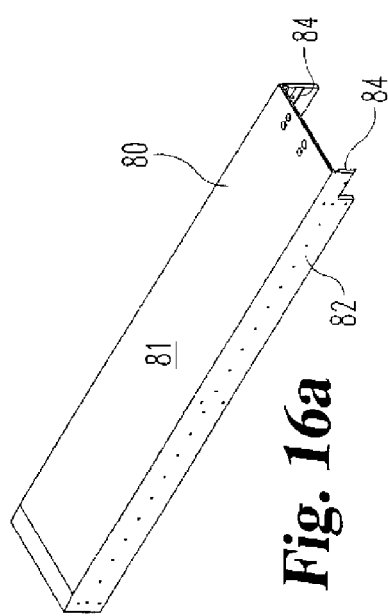
FIG. 16a is top perspective view of a left upper channel beam forming part of the floor assembly shown in FIG. 10.
Figure 16B:
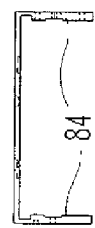
Figure 17B:
Figure 17A:
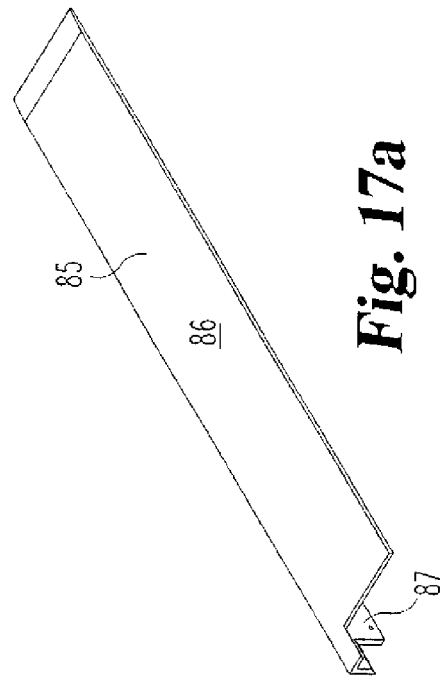
Figure 18:
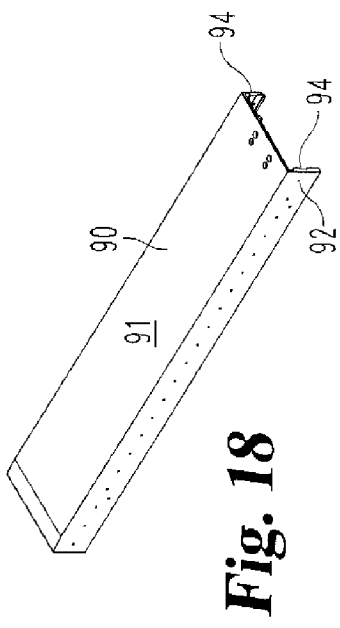
FIG. 18 is a top perspective view of a right upper channel beam forming part of the floor assembly shown in FIG. 10.
Figure 19A:
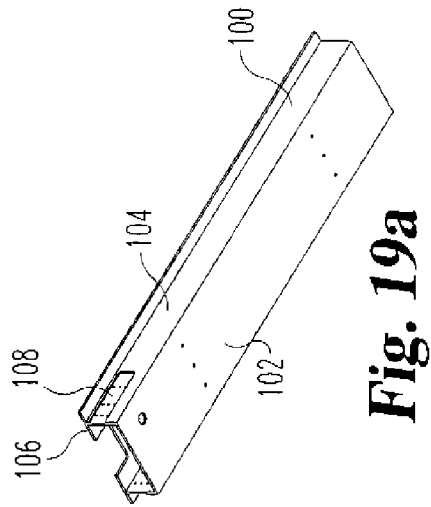
FIG. 19a is a bottom perspective view of a center lower channel beam forming part of the floor assembly shown in FIG. 10.
Figure 19B:
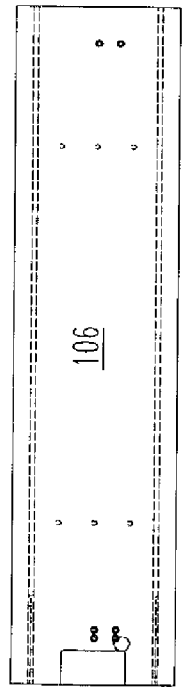
Figure 19C:
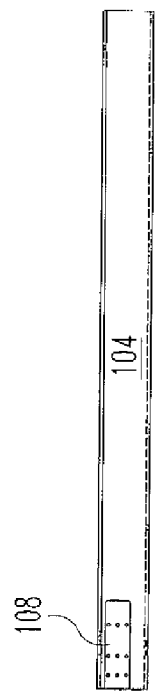
Figure 19D:
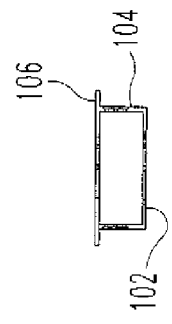
Figure 20B:
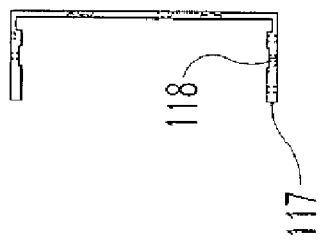
Figure 20A:
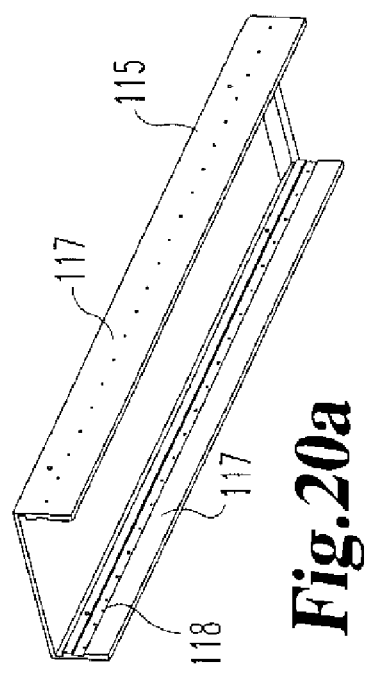
FIG. 20a is a bottom perspective view of a center upper channel beam supported by the center lower channel beam shown in FIGS. 19a-d.

As shown in FIGS. 16a-b and 18, the upper channel beams 80, 90 include side walls 84, 94 (one of which defines the attachment flange 82). The beams 80, 90 are thus in the shape of a U-shaped channel that fits outside the lower channel beam 70, as shown in FIG. 10. This same construction is implemented in the center movable panels, namely in the center lower channel beams 100 (FIGS. 19a-d) and center upper channel beams 115 (FIGS. 20a-b). The upper channel beams 115 include side walls 117 and an upper panel surface 119 that form the U-shape discussed above. The upper channel beam 115 thus fits over the lower channel beam 100, as shown in FIGS. 10 and 11a-d and particularly in the detail views of FIGS. 11c-d.

Each side wall 117 of the upper channel beam 115 includes a slot 118 running along the inside length of the channel. These slots are configured to receive a corresponding slide rail 112, as shown in FIG. 11c-d. The slide rails 112 fit within complementary configured bushings 110 mounted to the lower channel beam 100 at mounting recesses 108. The bushings and slide rails 110, 112, respectively, can be of known configuration to permit low friction movement of the upper channel beam 115 relative to the lower channel beam 100. In one embodiment, these components are formed of a polyurethane. The bushings and slide rails are sufficiently rigid to support the upper channel beam in a cantilevered manner as the upper channel beam extends from the lower channel beam, as shown in FIGS. 10 and 11a.

When the upper channel beam 115 is in its retracted position, as represented in FIG. 11d, the upper channel beam 115 is effectively supported by the lower channel beam 100. A plurality of support bushings or buttons (not shown) can be mounted to the panel surface 106 of the lower channel beam 100 to help bear the load of the upper channel beam 115.

Figure 21:
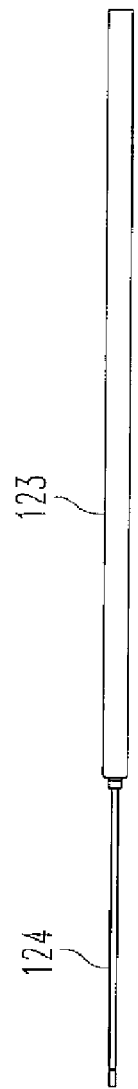
FIG. 21 is a side elevational view of a pneumatic cylinder mounted within the channels shown above that form the floor assembly.

In accordance with one aspect of the invention, the upper channel beams 80, 90 and 115 are translated (i.e., extended and retracted) relative to the corresponding lower channel beams 70 and 100, using an extension device 123, shown in FIG. 21. In the preferred embodiment, the extension device is a pneumatic cylinder that includes a piston rod 124. The piston rod 124 is connected to a corresponding latch mechanism 125 mounted to each upper channel beam 80, 90 and 115 (which of course means that every channel includes a corresponding cylinder 123). The cylinder 123 is mounted to the lower channel beams by a pair of mounting brackets 122, as depicted in FIGS. 11d-e. The throw or length of extension of the piston rod 124 is sufficient to span the distance between the floor assembly 20 and the latch beam 28 (FIG. 3). Thus, in the preferred embodiment, the cylinder 123 has a length of about 45 inches so the piston rod has a length of about 40 inches. As shown in FIG. 20a, the overall length of the upper channel beam 115 is almost 50 inches, so that at its greatest extension the upper channel beam overlaps the lower channel beam 100 by about 10 inches. The thickness of the support panel 119 of the upper channel beam is less than ½ inch, and more specifically about 0.29 inches, so the transition between the movable floor panel (115) and its fixed counterpart (100) is negligible.

In the preferred embodiment, the extension mechanism is a pneumatic cylinder. Other extendable mechanisms are contemplated, such as a hydraulic cylinder, an electromagnetic cylinder, a rack and pinion arrangement and other known mechanisms. The pneumatic cylinder is preferred since the treatment facility typically has a ready source of pressurized air. Moreover, leakage of a pneumatic cylinder is not problematic, as might be the case with a hydraulic cylinder.

The extension mechanism 123 performs a dual function. The first is to extend and retract the upper channel beams 80, 90, 115 relative to their corresponding lower channel beams 70, 100. The second is to release the latch mechanism 125 when it is desired to retract a previously extended floor panel. Consequently, in the preferred embodiment, the working end of the piston rod 124 is connected to the latch mechanism, as shown in FIG. 11c.

Figure 8A:
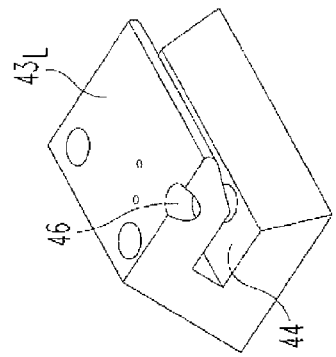
FIG. 8a is front perspective view of a left side latch that is mounted to the latch beam shown in FIGS. 6a-b.
Figure 8B:
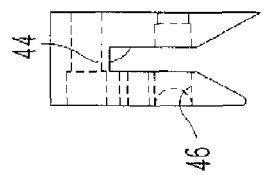

One embodiment of the latch mechanism 125 is shown in FIG. 22, with detail views of its components in FIGS. 23-27. Each movable floor panel or upper channel beam 80, 90 and 115 includes a latch mechanism. Each latch mechanism includes a tongue plate, such as the tongue plate configured for the position of the latch within the extendable panel assembly 24. In other words, the center panels include a tongue plate 127 (FIGS. 22, 25) that is configured to mate with a center latch 35 (FIG. 7a). Right tongue plate 145 (FIGS. 26a-b) mates with the right latch 43R (FIG. 9a), while the left tongue plate 150 (FIG. 27) is configured to engage the left latch 43L (FIG. 8a). Each tongue plate is sized to slide into the corresponding slots 36, 44 in the respective latches. The center tongue plate 127 defines a center notch 128 that engages the catch bolt 40 passing through the center bolt bore in the latch 35. The notches 146 and 151 of the outboard tongue plates are aligned to mate with the offset catch bolts in the outboard latches 43R, 43L. The edges of the tongue plates are configured to help guide the tongue plate into the corresponding latch slots. Similarly, the latch slots include beveled guide surfaces, such as surfaces 37 shown in FIG. 7d, to direct the tongues into the slots. With this construction, any drop in the position of the end of an extending floor panel is corrected and the panel regains its proper horizontal orientation in its locked position.

Figure 24B:
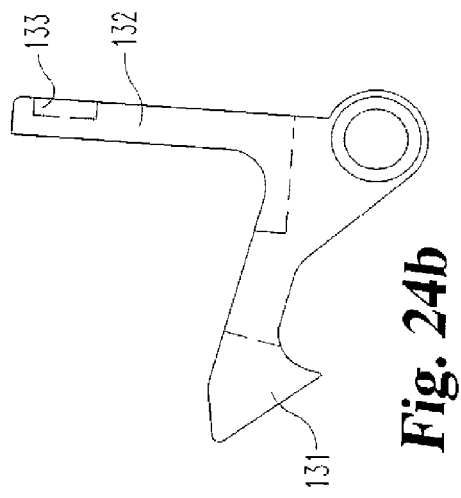
Figure 24A:
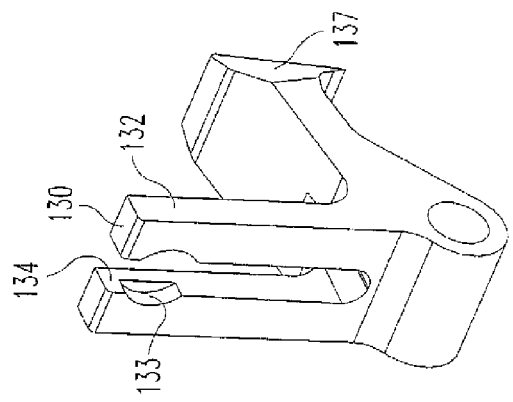
FIG. 24a is a perspective view of a latch member that forms part of the latch mechanism shown in FIG. 22.
Figure 26B:
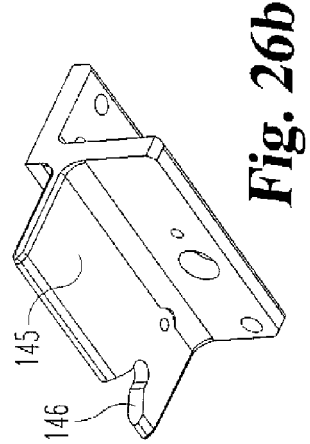
Figure 26A:
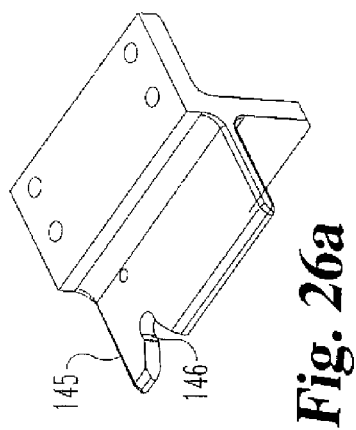
FIG. 26a is a top perspective view of a right tongue plate that forms part of a latch mechanism similar to that shown in FIG. 22.

Returning to FIG. 22, the latch mechanism 125 includes a support plate 129 that is generally perpendicular to the tongue plate 127. A latch member 130 is pivotably mounted to the tongue plate by a pivot bolt 139 so that the latch member is immediately adjacent the support plate. The latch member 130 includes a latch hook 131, as shown in FIGS. 24a-b, which is configured to engage the catch bolts 40 in the latches 35, 43R and 43L. A fulcrum plate 132 is situated generally perpendicular to the latch hook. The fulcrum plate defines a spring recess 133 at its end that contains the end of a biasing spring 140 (FIG. 22). The biasing spring operates on the fulcrum plate 132 to pivot the latch hook 131 into its locked position. As a movable panel approaches the latch beam, the outside edge of the latch hook 131 contacts the catch bolt so that the latch member 130 pivots against the force of the spring 140 until the bolt is snagged by the latch hook. The spring 140 exerts a constant force against the fulcrum plate 132 to maintain pressure between the latch member 130 and the catch bolt 40.

Figure 23:
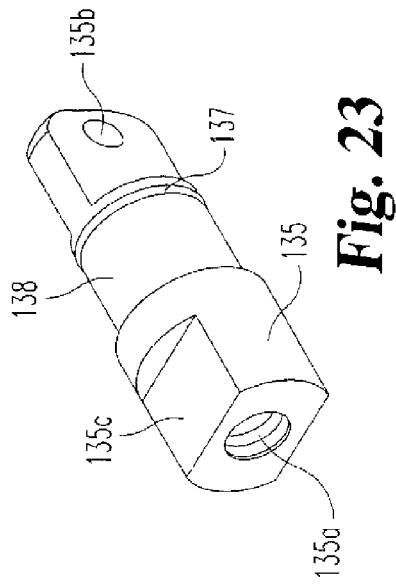
FIG. 23 is a perspective view of a cylinder clevis that forms part of the latch mechanism shown in FIG. 22.
Figure 25:
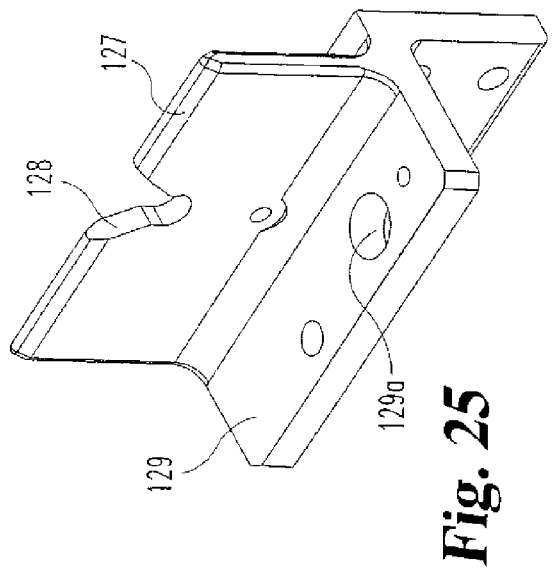
FIG. 25 is a perspective view of a center tongue plate that forms part of the latch mechanism shown in FIG. 22.

The fulcrum plate 132 also defines a clevis slot 134 through which an end of a cylinder clevis 135 (FIG. 23) extends. The clevis 135 includes a bore 135b that receives a clevis pin 136. The pin bears against the fulcrum plate 132, especially when the clevis is retracted relative to the support plate 129. As shown in FIG. 23, the body 135c of the clevis defines a bore 135a that is configured to mate with the working end of the piston rod 124 of the extension mechanism or cylinder 123. The body 135b is larger than the clevis bore 129a (FIG. 25) in the support plate so that the body bears against the support plate 127 when the piston rod is extended. The clevis includes a shaft portion 138 that is sized to fit through the bore 129a. A snap ring 137 engages the shaft portion 138 to thereby trap the clevis within the bore 129a. It is understood that the travel of the clevis relative to the support plate 129 is limited at one end by the body 135c and at the other end by the snap ring 137.

The movable floor panels are extended by activating the cylinder 123. As the cylinder is pressurized, the piston rod 124 extends, pushing the clevis 135 to which it is connected. As the piston rod moves, the clevis body 135c bears against the support plate 129 of the latch mechanism 125. Since the latch mechanism is fastened to the upper channel beam (80, 90, 115), the channel or floor panel moves toward the fixed floor F. When the piston rod pushes the latch mechanism, the clevis pin 136 is at its farthest position from the support plate 129 and in this position only serves to prevent over-rotation of the latch hook 131 under the force of spring 140. As explained above, when the tongue plate reaches the corresponding latch, the catch bolt pivots the latch member 130 until the latch hook locks around the catch bolt. Again, the spring 140 maintains the latch hook in solid engagement with the catch bolt.

An adjustment screw 142 may be provided passing through the support plate as shown in FIG. 22. The adjustment screw includes a pressure face 143 that bears against the latch beam 28 to provide a counter-force against the effort of the latch hook 131 to draw the catch bolt toward the latch member. All of the components of the latch mechanism 125 and latches 35, 43 cooperate to provide a solid and positive engagement between the extended floor panel and the stationary floor.

When it is desired to retract the upper channel beam 115 each latch mechanism 125 must be released from the latch beam 28. When a retract command is directed to each cylinder 123, the piston rod is retracted. As the rod retracts, the clevis pin 136 pulls on the fulcrum plate 132 against the force of the spring 140. By the time the snap ring 137 has contacted the support plate 129, the latch member 130 has pivoted enough so that the latch hook 131 has disengaged the catch bolt 40. The latch mechanism is then released from the latch beam 28.

Continued return movement of the piston rod now pulls on the support plate 129, latch mechanism 125, and ultimately the upper channel beam floor panel 115. When the piston rod 124 reaches the end of its stroke, the upper channel beam 115 is properly positioned over the lower channel beam 100. It can thus be appreciated that the extension mechanism 123 and the latch mechanism 125 provide means for not only extending and retracting a floor panel, but also for automatically latching and un-latching a movable floor panel from the latch beam 28 connected to the fixed floor F.

In accordance with the present invention, a control system is provided that directs the activity of each movable floor panel. Thus, in the illustrated embodiment, the control system determines whether and when any of the seven center panels 115 or either of the two end panels 80, 90 (with their associated wing panels 75, 85) are extended or retracted. The control system can include a pneumatic controller that is connected to all nine of the pneumatic cylinders, wherein the controller includes an array of valves that either provides pressurized air to or bleeds the air from the cylinder. The cylinder control valves are preferably electronically controlled from electrical signals generated by a microprocessor or electronic controller. The control system thus coordinates the operation of these cylinder control valves to thereby extend or retract the respective panel(s).

It is understood that important goals of the floor assembly 20 of the present invention include: 1) providing a floor surface within the gantry enclosure adjacent the end of the patient table; 2) providing a floor connection or path between the floor surface within the gantry enclosure and the fixed floor of the treatment facility; and 3) preventing collisions between the rotating gantry and floor panels of the assembly 20 that may be extended as the gantry approaches. The structural aspect of the invention described above accomplish the first two goals.

The third goal is accomplished by software or firmware within the control system. Preferably, the gantry 12 is provided with sensors (not shown) that relay the exact angular position of the nozzle 15 (FIG. 1) relative to the floor assembly 20. During certain treatment procedures, a technologist or technician will issue a command to rotate the gantry from one angular position to another. In other procedures, the gantry may move according to a pre-determined program. In accordance with the present invention, the control system determines whether an upcoming move of the gantry will cause a collision with an extended floor panel. In particular, the control system knows the angular position of each movable floor panel when it is extended, the current angular position of the gantry, and the ending angular position of the gantry after its expected rotation. If the angular position of an extended movable floor panel falls within the current and ending angular position of the gantry, a conflict exists. If so, the control system issues a signal to the pneumatic valve of the appropriate pneumatic cylinder to retract the associated floor panel or upper channel beam 80, 90 or 115.

At the same time, the control system may also assess whether retracting the particular panel will eliminate a path between the movable floor 20 and the fixed floor F. It is desirable to always maintain such a path, even during rotation of the gantry, so that medical personnel can have ingress or egress. If the assessment shows that no current floor path exists, the control system makes a determination as to which movable floor panels can be extended without conflicting with the rotation of the gantry, and then issues an extension command to an appropriate cylinder. As desired, multiple floor panels can be extended, although the control system is preferably configured to prevent all of the floor panels being extended at the same time.

In certain embodiments, the floor movement protocol is automated, requiring human intervention only in the event of an anomaly or emergency. In one embodiment, all movements of the movable panels are orchestrated and timed with the rotational movement of the gantry and nozzle. For instance, in one specific example, the two left-most panels are extended as the gantry approaches during a clockwise rotation. As the gantry passes beneath the patient table, the left-most panels are retracted and the two right-most panels are extended so that a path is always maintained. The rate of extension and retraction of the panels can be calibrated to the rate of rotation of the gantry.

However, in the most preferred embodiment of the invention, every movement of the gantry and the floor apparatus requires human intervention to acknowledge and accept the proposed movement. In this way, any potentially unsafe movement can be prevented by the human operator at the treatment room. The human operator may be in a separate control room, and/or may be at the gantry itself. In the latter case, a remote actuator device, or hand pendant, can be provided that communicates with the control system. Thus, in this preferred embodiment, the operator enters a movement command to the control system which then determines and displays any conflicts with the movable floor panels. The control system may also display the suggest panel move sequence for approval by the operator.

In the preferred embodiment, the control system includes a computer display that may be used to notify the human operator of the status of the system and the proposed gantry and floor panel movements. A variety of GUIs can be implemented to communicate this information in an easily interpreted manner and to permit essentially fail-safe communication of movement commands through the human operator.

The control system is also preferably configured to implement various safety restrictions. For instance, the controller may be operable to prevent extension of all floor panels at one time. Other restrictions may include: 1) preventing simultaneous movement of multiple panels; 2) simultaneous retraction of all panels; 3) enforced limits as to the minimum number of panels that must be extended and latched at all times; 4) immediate stop of extension or retraction of a floor panel, regardless of the position of the panel; and 5) emergency overrides of any movement command in a sensed emergency condition or due to human intervention.

It is contemplated that the control system is a microprocessor based system and that the various controls discussed above may be implemented in software. The control system for the retractable floor of the present invention may be integrated into the control system for the radiation therapy facility. In some instances, a pre-programmed treatment plan may incorporate move commands for the gantry as well as for the retractable floor.

As explained above, the present invention contemplates a retractable floor system that can be positioned within a rotating gantry in a radiation treatment facility. The retractable floor system is configured to surrounding a patient table within the gantry and to provide a path between the fixed floor of the treatment facility and the patient table. The retractable floor system includes extendable/retractable panels, each having a latch configured to latch the panel to the fixed floor when in the extended position. The retraction mechanism automatically releases the latch when it is desired to retract the panel.

Each retractable panel is driven by a simple actuator, such as a pneumatic cylinder and each cylinder can be controlled by an electrically activated valve. Each valve is in turn controlled by the control system for the retractable floor, which preferably implements software programs to direct when a particular valve is activated to either extend or retract the corresponding cylinder and associated movable floor panel.

In accordance with the preferred embodiment, the movable floor system follows certain criteria primarily dictated by safety concerns. These criteria include:

a) The retractable floor assembly within the gantry enclosure is capable of supporting the weight of at least two average sized adults;

b) The floor assembly permits rotation of the gantry from −185° to the +185°;

c) The floor panels of the assembly remain level with the fixed treatment room floor at all times, including during gantry rotation;

d) The floor panels mechanically latch to the fixed treatment room floor when fully extended;

e) The mechanical latch is configured so that the floor panels cannot be unintentionally released by personnel or equipment moving across the floor panels;

f) There is no vertical step between adjacent floor panels or between the extended floor panels and the fixed floor;

g) The interface between non-movable and movable floor segments is minimal, not exceeding ½ inch, with the segments configured so that the step down is from a movable segment to a non-movable segment;

h) The control system for the movable floor panels prevents all of the movable floor panels from being in their retracted position at the same time;

i) The control system mandates that at least two moveable panels are extended and locked to the fixed treatment room floor at all times during non-emergency operation;

j) The control system is configured to automatically stop the extension or retraction of a floor panel at the onset of certain emergency events;

k) The control system for the retractable floor system can be used to retract selected floor panels as needed to permit line of sight between an X-ray tube and its associated DR panel;

l) The control system may include a manual override feature that can be activated at the control panel in the control room to allow direct control over the extension or retraction of any of the movable floor panels;

m) The control system inhibits movement of a selected floor panel until the pending movement is acknowledged by the human operator at the control panel, except in the case of an emergency movement;

n) Certain technicians or medical personnel may be provided with a remote activation device that can be used to initiate movement of a floor panel;

o) The control system includes software that evaluates a gantry move to determine whether and which floor panels must be retracted or extended and when the movement must occur to permit passage of the nozzle;

p) As a consequence, the gantry may be provided with position sensors that are read by the control system to determine the angular position of the gantry, and particularly of the nozzle, at all times;

q) Control of gantry rotation is not disturbed by the control system for the present invention, meaning that the radiation technologist maintains direct control of the gantry rotation regardless of which technician controls the retractable floor;

r) In certain embodiments, a requested gantry rotation may be only enabled by a technologist using the remote activation device at the gantry entrance;

s) In certain embodiments, a request for gantry rotation between two angles that do not require movement of a floor panel can proceed under direct control of the technologist without any commands by the control system for the retractable floor;

t) When a gantry rotation request requires movement of one or more floor panels to avoid collision with the nozzle, a display may be generated at the control room describing which floor panels are to move, and the remote activation device may be enabled only after the display has been acknowledged by a technologist at the control panel once the technologist has determined that no equipment or personnel will be harmed by the floor movement or the gantry rotation;

u) When an X-ray is requested as part of the treatment protocol, a determination is made whether a floor panel must be moved, in which case an alert display is generated in the control room which must be acknowledged before the remote activation device is enabled to control retraction of a floor panel;

v) Once the X-ray request has been completed, another alert display at the control room is generated to permit extension of the previously retracted floor panel by operation of the remote activation device;

w) The control system can be password driven to ensure that only specially qualified personnel can make gantry and floor movement commands.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

What is claimed is:

1. A floor system for use with a rotating gantry in a radiation treatment facility comprising:
   a carriage assembly configured to be slidably supported within the gantry to maintain a substantially constant orientation while the gantry is rotating; and
   an extendable/retractable panel assembly supported on said carriage assembly, said panel assembly including a plurality of non-movable floor panels and a like plurality of movable floor panels slidably mounted over corresponding ones of said non-movable panels to extend outside said carriage assembly, said movable panels sized to span a distance between said carriage assembly and a fixed floor of the treatment room and each of said movable panels having a platform surface for supporting a person thereon.

2. The floor system of claim 1, wherein said carriage assembly includes a plurality of rollers arranged to contact the gantry so that said rollers rotate as the gantry is rotated to maintain said carriage assembly in said substantially constant orientation.

3. The floor system of claim 1, wherein each of said movable panels includes a latch mechanism configured to automatically engage a mating latch component attached to the fixed floor of the treatment room.

4. The floor system of claim 3, wherein said latch mechanism is configured to automatically disengage said mating latch component as said movable panel is retracted.

5. A floor system for use with a rotating gantry in a radiation treatment facility, comprising:
   a carriage assembly configured to be slidably supported within the gantry to maintain a substantially constant orientation while the gantry is rotating; and
   an extendable/retractable panel assembly supported on said carriage assembly, said panel assembly including a plurality of non-movable floor panels and a like plurality of movable floor panels slidably mounted over corresponding ones of said non-movable panels, said movable panels sized to span a distance between said carriage assembly and a fixed floor of the treatment room and each of said movable panels having a platform surface for supporting a person thereon, wherein said panel assembly includes an actuator mounted between each of said plurality of non-movable floor panels and a corresponding one of said movable panels, said actuator configured to extend and retract said movable panel relative to said non-movable panel.

6. The floor system of claim 5, wherein said actuator includes a pneumatic cylinder supported by said non-movable panel and a piston rod connected to said movable panel, said piston rod extendable and retractable from said cylinder to extend and retract said movable panel relative to said non-movable panel.

7. The floor system of claim 6, wherein each of said movable panels includes a latch mechanism configured to automatically engage a mating latch component attached to the fixed floor of the treatment room.

8. The floor system of claim 7, wherein said piston rod is connected to said latch mechanism so that said piston rod is operable when retracted to disengage said latch mechanism from said mating latch.

9. The floor system of claim 8, wherein said latch mechanism includes a latch hook configured to engage said mating latch, and said piston rod is connected to said latch hook and is operable to disengage said latch hook from said mating latch.

10. The floor system of claim 5 further comprising a control system operable to control said actuator of each of said plurality of movable panels to selectively extend or retract said movable panels.

11. The floor system of claim 10, wherein said control system includes software that is operable to control said actuator of each of said plurality of movable floor panels in response to the rotation of the gantry.

12. The floor system of claim 11, wherein said software of said control system is operable to evaluate a planned rotational movement of the gantry to determine whether the movement will cause a collision with an extended floor panel and then to control said actuator of each of said extended floor panel to retract said panel.

13. The floor system of claim 11, wherein said software of said control system is operable to control said actuator of each of said plurality of movable floor panels so that at all times during rotation of the gantry least one movable floor panel is in its extended position.

14. The floor system of claim 1, wherein each of said plurality of non-movable floor panels has a platform surface for supporting a person thereon.

15. The floor system of claim 1, wherein said panel assembly includes a bearing interface between each of said plurality of non-movable floor panels and said corresponding plurality of movable floor panels.

16. A floor system for use with a rotating gantry in a radiation treatment facility comprising:
   a carriage assembly configured to be slidably supported within the gantry to maintain a substantially constant orientation while the gantry is rotating;
   a panel assembly supported on said carriage assembly, said panel assembly including a plurality of movable floor panels, each of said movable floor panels having a platform surface for supporting a person thereon; and
   an actuator associated with each of said plurality of movable floor panels operable to move the panel from a retracted position to an extended position outside said carriage assembly spanning a distance between said carriage assembly and a fixed floor of the treatment facility.

17. The floor system of claim 16, wherein said carriage includes a plurality of rollers arranged to contact the gantry so that said rollers rotate as the gantry is rotated to maintain said carriage assembly in said substantially constant orientation.

18. The floor system of claim 16, wherein each of said plurality of movable panels includes a latch mechanism configured to automatically engage a mating latch component attached to the fixed floor of the treatment room.

19. The floor system of claim 16, wherein said actuator is a pneumatic cylinder having a piston rod connected to said movable floor panel.

20. The floor system of claim 19, further comprising a control system operable to control said actuator of each of said plurality of movable floor panels to selectively extend or retract said movable panels.

* * * * *